United States Patent
Ihde, II

(10) Patent No.: US 9,205,469 B2
(45) Date of Patent: *Dec. 8, 2015

(54) FLUID ABSORBENT SURGICAL DEVICE FOR CANNULAS

(71) Applicant: Glenn M. Ihde, II, Red Oak, TX (US)

(72) Inventor: Glenn M. Ihde, II, Red Oak, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/279,739

(22) Filed: May 16, 2014

(65) Prior Publication Data

US 2014/0245549 A1  Sep. 4, 2014

Related U.S. Application Data

(63) Continuation of application No. 13/151,240, filed on Jun. 1, 2011, now Pat. No. 8,764,783, which is a continuation-in-part of application No. 11/848,896, filed on Aug. 31, 2007, now Pat. No. 8,480,699.

(60) Provisional application No. 60/841,963, filed on Sep. 1, 2006.

(51) Int. Cl.
*A61B 17/34* (2006.01)
*B08B 9/043* (2006.01)
*A61B 19/00* (2006.01)
*A61B 1/12* (2006.01)

(52) U.S. Cl.
CPC ............ *B08B 9/0436* (2013.01); *A61B 17/3421* (2013.01); *A61B 19/34* (2013.01); *A61B 1/121* (2013.01); *A61B 1/126* (2013.01); *A61B 17/3462* (2013.01); *A61B 2017/3437* (2013.01); *Y10T 29/49826* (2015.01)

(58) Field of Classification Search
CPC ............. B08B 9/0436; A61B 17/3421; A61B 17/3462; A61B 19/34; A61B 2017/3437; A61B 1/121; A61B 1/126; Y10T 29/49826
USPC .......................... 606/185; 15/104.05; 29/428
See application file for complete search history.

(56) References Cited

U.S. PATENT DOCUMENTS

| | | | |
|---|---|---|---|
| 724,913 A * | 4/1903 | Montgomery ................. | 604/278 |
| 3,149,360 A | 9/1964 | Lend | |
| 3,818,911 A | 6/1974 | Fournier | |
| 3,850,754 A | 11/1974 | Wilkins et al. | |
| 5,084,005 A | 1/1992 | Kachigian | |
| 5,147,288 A | 9/1992 | Schiavo | |
| 5,188,630 A | 2/1993 | Christoudias | |
| 5,339,828 A | 8/1994 | Keating et al. | |
| 5,392,766 A | 2/1995 | Masterson et al. | |

(Continued)

FOREIGN PATENT DOCUMENTS

WO    2008028187 A2    3/2008

OTHER PUBLICATIONS

Foreign Communication from a Related Counterpart Application—International Search Report and Written Opinion, PCT/US22007/077532, Mar. 17, 2008, 10 pages.

(Continued)

*Primary Examiner* — Tuan V Nguyen
*Assistant Examiner* — Tin Nguyen

(57) ABSTRACT

A surgical instrument that absorbs fluid material on surfaces of a trocar is provided. The surgical instrument comprises a handle having at least two ends and an absorbent area at a first end of the handle. The absorbent area comprises a plurality of absorbent discs and a plurality of spacers.

20 Claims, 15 Drawing Sheets

(56) References Cited

U.S. PATENT DOCUMENTS

| | | | |
|---|---|---|---|
| 5,407,423 | A | 4/1995 | Yoon |
| 5,518,502 | A | 5/1996 | Kaplan et al. |
| 5,599,292 | A | 2/1997 | Yoon |
| 5,700,239 | A * | 12/1997 | Yoon ............... 604/2 |
| 5,715,559 | A | 2/1998 | Mitri |
| 6,277,090 | B1 | 8/2001 | Crawford, Jr. |
| 6,565,544 | B1 * | 5/2003 | Rainin ............... 604/313 |
| 6,923,760 | B2 | 8/2005 | Koda et al. |
| 7,112,184 | B2 | 9/2006 | Bichsel et al. |
| 7,211,061 | B1 | 5/2007 | Maxwell |
| 8,480,699 | B2 | 7/2013 | Ihde |
| 8,764,783 | B2 | 7/2014 | Ihde, II |
| 2003/0181840 | A1 | 9/2003 | Tsaur |
| 2004/0204671 | A1 | 10/2004 | Stubbs et al. |
| 2006/0003182 | A1 | 1/2006 | Lane et al. |
| 2006/0084983 | A1 | 4/2006 | Kim |

OTHER PUBLICATIONS

Foreign Communication from a Related Counterpart Application—International Preliminary Report on Patentability, PCT/US22007/077532, Mar. 12, 2009, 8 pages.

Office Action dated Sep. 28, 2010, U.S. Appl. No. 11/848,896.

Final Office Action dated Mar. 16, 2011, U.S. Appl. No. 11/848,896.

Notice of Allowance dated Mar. 14, 2013, U.S. Appl. No. 11/848,896.

FAIPP Pre-Interview Communication dated Jun. 20, 2013, U.S. Appl. No. 13/151,240, filed Jun. 1, 2011.

FAIPP Office Action dated Sep. 4, 2013, U.S. Appl. No. 13/151,240, filed Jun. 1, 2011.

Notice of Allowance dated Feb. 18, 2014, U.S. Appl. No. 13/151,240, filed Jun. 1, 2011.

Ihde II, M.D., Glenn M., Patent Application entitled "Fluid Absorbent Surgical Device for Cannulas", filed Jul. 16, 2014, U.S. Appl. No. 14/333,508.

* cited by examiner

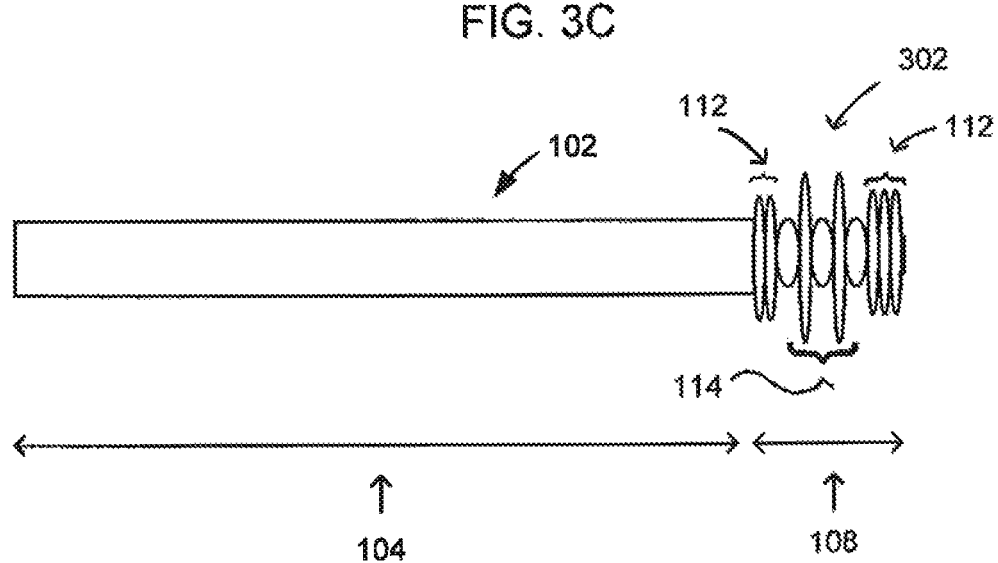

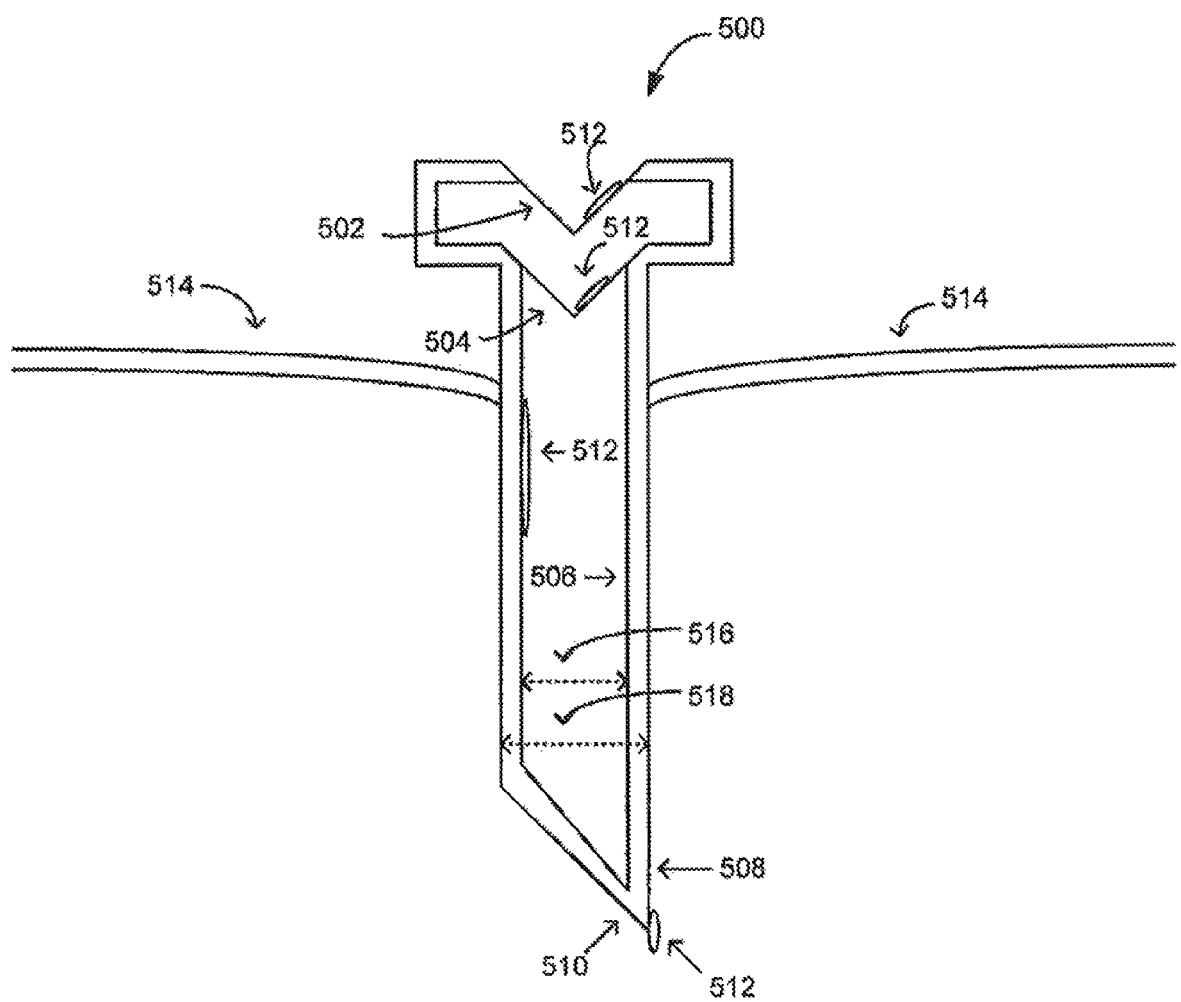

FLUID ABSORBENT SURGICAL DEVICE FOR CANNULAS

CROSS-REFERENCE TO RELATED APPLICATIONS

This application is a continuation of U.S. patent application Ser. No. 13/151,240 filed Jun. 1, 2011, which is a continuation-in part of U.S. patent application Ser. No. 11/848,896 filed Aug. 31, 2007, which claims the benefit of U.S. Provisional Application 60/841,963 filed Sep. 1, 2006, the disclosures which are hereby incorporated by reference.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Laparoscopic surgery is a form of minimally invasive, endoscopic surgery performed in the abdomen. With laparoscopic surgery, general anesthesia is given. A small incision is usually made below or inside the umbilicus. The abdomen is then insufflated with an inert gas, such as carbon dioxide, by inserting a special needle or a trocar through the umbilicus. A trocar, also called a trocar sleeve or cannula, is a specially designed tube, usually 5 or 10 mm in diameter, with a valve through which a surgeon can insert special instruments. Insufflation induces a state of pneumoperitoneum, which enhances the surgeon's view and ability to make manipulations. If a special needle is used, the surgeon removes the needle after an adequate volume of gas is insufflated into the abdominal cavity and inserts a trocar. The valve in the trocar prevents the inert gas from escaping through the trocar. This helps to maintain the state of pneumoperitoneum. An endoscope, also called a laparoscope, is then placed through the trocar. The laparoscope allows the surgeon to visualize the pelvic and abdominal organs on a video monitor. Additional smaller incisions are made in the abdomen to allow placement of additional trocars as needed. The additional trocars are for the surgeon to place specially designed surgical instruments into the abdominal cavity, allowing the surgeon to carry out the same procedure as in open surgery.

For patients, the advantages of laparoscopic surgery over open surgery include reduced trauma to the body, reduced blood loss, and smaller surgical scars. Patients also leave the hospital sooner after laparoscopic and return to normal activities sooner than with conventional open surgery. Similar minimally invasive approaches, such as thoracoscopic surgery, may be performed on other areas of the body. These approaches share some of the same advantages and challenges as laparoscopic surgery.

SUMMARY

These and other features will be more clearly understood from the following detailed description taken in conjunction with the accompanying drawings and claims.

In an embodiment of the disclosure, a system for absorbing fluid material on trocar surfaces is provided. The system comprises a trocar and a cleaning instrument having at least two ends with an absorbent area at one end of the cleaning instrument. The absorbent area has a first outer diameter at a first part of the absorbent area and a second smaller outer diameter at a second part of the absorbent area, such that at least a portion of the absorbent area has an outer diameter larger than an inner diameter of the trocar. When the absorbent area is inserted inside the trocar, the absorbent area comes into contact with an inner wall of the trocar and absorbs fluid along the inner wall. Furthermore, when a part of the absorbent area is passed through a tip at the distal end of the trocar, the absorbent area absorbs fluid along an outer wall of the tip.

In another embodiment of the disclosure, a method of absorbing fluid material on a surface of a trocar is provided. The method comprises inserting an absorbent area of a cleaning instrument inside the trocar, the absorbent area having an outer diameter larger than an inside diameter of the trocar. When the absorbent area is inserted inside the trocar, the absorbent area comes into contact with an inner wall of the trocar and absorbs fluid along the inner wall. Also, when a part of the absorbent area is passed through a tip at the distal end of the trocar, the absorbent area absorbs fluid along an outer wall of the tip. Furthermore, the absorbent area does not come into significant contact with bodily fluid that is not gathered on the inner or outer wall of the trocar.

In another embodiment of the disclosure, a method of creating a surgical instrument is provided. The method comprises providing an absorbent area on at least one end of a handle, the absorbent area comprising a plurality of absorbent discs with one or more of the absorbent discs forming a first part of the absorbent area having an outer diameter that approximates an inside diameter of a trocar and one or more of the absorbent discs forming a second part of the absorbent area having an outer diameter that is at least the outer diameter of the trocar. The method further comprises inserting the absorbent area into the trocar having an inner wall, an outer wall, and distal end. The method also comprises absorbing fluid along the inner wall of the trocar using the edges of at least one of the plurality of absorbent discs absorb fluid. The method further comprises inserting at least one of the absorbent discs forming the absorbent area through a tip at the distal end of the trocar and absorbing fluid along the outer wall of the trocar at the tip of the distal end of the trocar using at least one of the absorbent discs inserted through the tip at the distal end of the trocar.

In another embodiment of the disclosure, a surgical instrument that absorbs fluid material on surfaces of a trocar is provided. The surgical instrument comprises a handle having at least two ends and an absorbent area at a first end of the handle. The absorbent area comprises a plurality of absorbent discs and a plurality of spacers.

In another embodiment of the disclosure, a surgical instrument that absorbs fluid material on surfaces of a trocar is provided. The surgical instrument comprises a handle having at least two ends and an absorbent area at a first end of the handle. The absorbent area comprises a plurality of absorbent discs and the plurality of absorbent discs approximate an inner diameter of the trocar.

In another embodiment of the disclosure, a method of creating a surgical instrument is provided. The method comprises providing an absorbent area on at least one end of a handle, the absorbent area comprising a plurality of absorbent discs. The method further comprises separating each of the plurality of absorbent discs with at least one spacer.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

FIGS. 3A to 3C illustrate embodiments of the disclosure having an absorbent area at one end of the surgical device.

FIG. 5 depicts fluid materials on the surfaces of a trocar inserted across an abdominal wall.

DETAILED DESCRIPTION

Figure 1A:
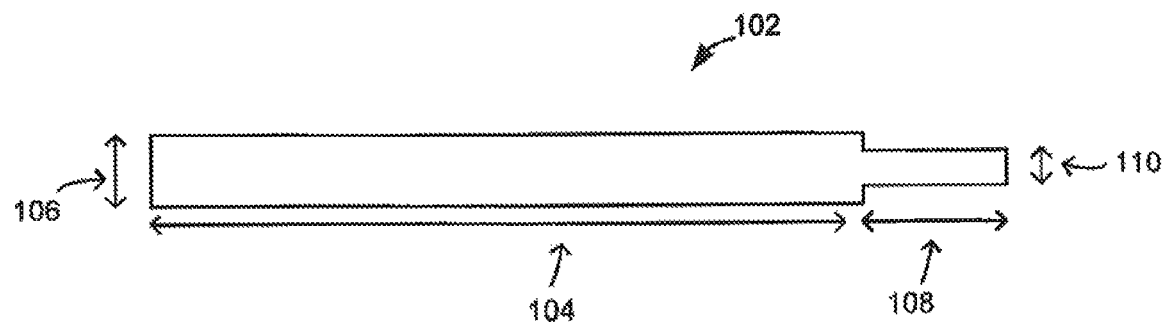
FIGS. 1A to 1D illustrate the components of a surgical device according to an embodiment of the disclosure.

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

The key element in laparoscopic surgery is the use of a laparoscope to view and illuminate the operative field. The laparoscope comprises a telescopic rod lens system that is connected to a video camera (single chip or three chip). The rod is made of a light conducting material that is used to pass the image from the tip of the rod to the camera head. The rod is passed through the trocar and into the abdominal cavity where it transmits the light and images from inside the abdomen to the camera. The camera then transmits the light and images to a video monitor for viewing.

When the laparoscope passes through the trocar, fluid materials deposited on the trocar during insertion have a tendency to pass onto the lens of the laparoscope and obscure the view of the camera. Fluid materials can pass onto the lens as it passes through a valve. Fluid materials can also pass onto the lens, for example, as it passes through the inner walls of the trocar. Fluid materials along the inner walls and the tip of the trocar can transfer to the lens by way of capillary action due to the fluid material's surface tension.

When fluid materials obscure the lens, the laparoscope must be removed from inside the trocar, and the lens is cleaned outside of the abdominal cavity. However, as long as fluid materials remain inside the trocar, the lens will become obscured immediately upon re-insertion into the trocar. Again, the laparoscope will then be removed from inside the trocar, and the lens cleaned outside of the abdominal cavity. This process is repeated several times until the lens no longer becomes obscured with fluid materials. Cleaning the lens repeatedly until it no longer becomes obscured with fluid materials increases the total time that it takes to perform the laparoscopy. This increases the amount of time that the patient is under anesthesia as well as the amount of time the instruments are inside the abdominal cavity without being directly visualized.

Accordingly, the disclosure teaches a surgical device for keeping a laparoscopic lens free of obstructing fluid materials by absorbing fluid material from the surfaces of the trocar. The surgical device includes an absorbent area that absorbs fluid material from the surfaces of the trocar, including the valves, the inner wall, a distal tip of the trocar, and an outer wall of the trocar. In one embodiment, the absorbent area comprises a plurality of sterile cotton discs. The plurality of sterile cotton discs comprises a first group of discs with a diameter slightly larger than the inside diameter of the trocar and a second group of discs with a diameter slightly larger than the outside diameter of the trocar. When the absorbent area of the surgical device is inserted inside the trocar, the absorbent area absorbs fluid material along any valve that it passes through and along the inner wall of the trocar. The absorbent area also absorbs fluid material along the outer wall of the trocar as it passes through the tip of the trocar. In some embodiments, the absorbent area also incorporates one or more beads to separate some of the discs to allow flexibility along the edges.

Because the surgical device of the disclosure absorbs fluid material from inside the trocar, it may be used to reduce the number of passes needed to remove fluid materials from the laparoscopic lens. Reducing the number of passes reduces the total time that it takes to perform the laparoscopy, which reduces the amount of time that the patient is under anesthesia as well as the amount of time the instruments are inside the abdominal cavity without being directly visualized.

FIGS. 1A to 1D illustrate the components of a surgical device according to an embodiment of the disclosure. FIG. 1A depicts a handle 102. The handle 102 is made, for example, of a type of plastic that is commonly used in many surgical instruments. The handle 102 is shown as having a first part 104, which has a first diameter 106, and a second part 108, which has a second diameter 110. In this embodiment, the first part 104 has a larger diameter than the second part 108. For example, in one embodiment, the first part 104 of the handle may be approximately 30 cm. in length with a diameter of 4 mm. The second part 108 may be approximately 6 cm. in length with a diameter of 2 mm.

Figure 1B:
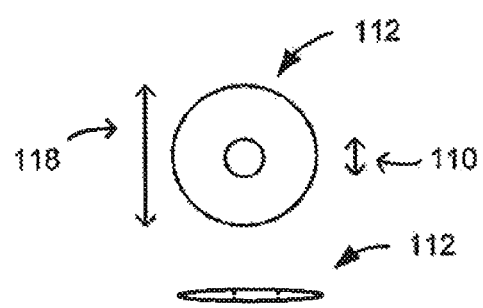
Figure 1C:
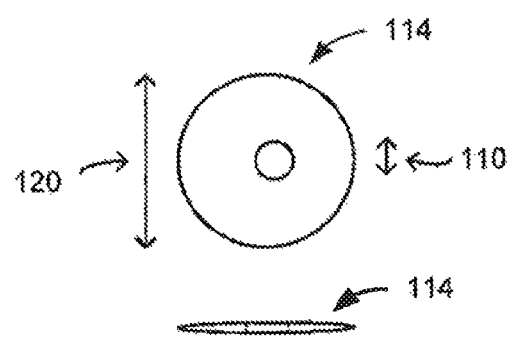
Figure 1D:
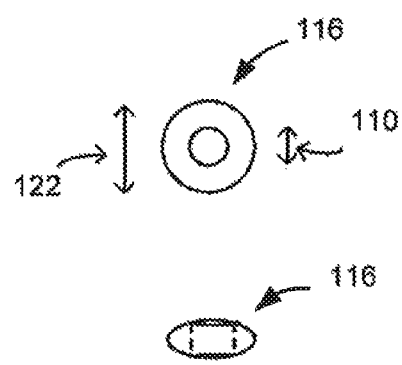

Top and side views of a first absorbent disc 112 is shown in FIG. 1B. FIG. 1C shows a second absorbent disc 114, and FIG. 1D shows a spacer 116. The first absorbent disc 112 and the second absorbent disc 114 are made, for example, of sterile cotton, and the spacer 116 is a bead made of a type of plastic that is commonly used in many surgical instruments. The term "disc" refers to a generally circular object with a height or a thickness that is less than its total diameter, i.e. any generally circular object with some amount of dimensional flattening to make it less than a perfect sphere. In this embodiment, the first absorbent disc 112, the second absorbent disc 114, and the spacer 116 have an inner diameter that is approximately the same as the second diameter 110 of the second part 108. The first absorbent disc 112 is shown as having an outer diameter 118, the second absorbent disc 114 is shown as having an outer diameter 120, and the spacer 116 is shown as having an outer diameter 122. In this embodiment, the outer diameter 120 of the second absorbent disc 114 is larger than the outer diameter 118 of the first absorbent disc 112 with the spacer 116 having the smallest outer diameter 122. The first absorbent disc 112 and the second absorbent disc 114 have roughly the same thickness, and the spacer 116 has a significantly greater thickness than the first absorbent disc 112 and the second absorbent disc 114. For example, in one embodiment, the inner diameter of the first absorbent disc 112, the second absorbent disc 114, and the spacer 116 would be the same as the diameter of the second part 108, i.e. 2 mm. to allow placement onto the second part 108. The first absorbent disc 112 would have an outer diameter 118 of approximately 6 mm. The second absorbent disc 114 would have an outer diameter 120 of approximately 7 mm. The spacer 116 would have an outer diameter 122 of approximately 4 mm. and a thickness of approximately 1 mm. Such dimensions could be implemented, for example, for use with a trocar having a 5 mm. inner diameter.

Figure 2A:
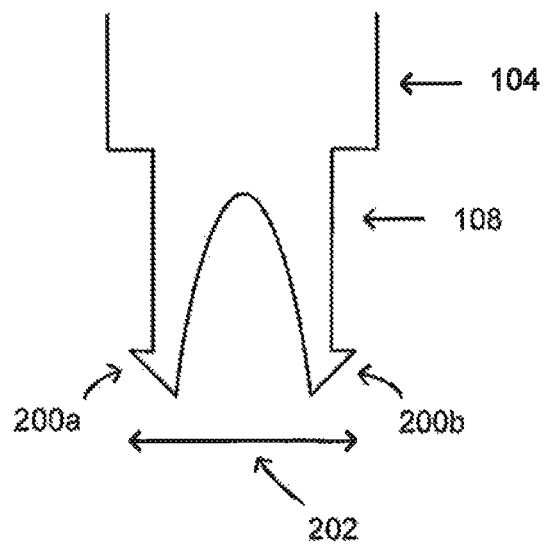
FIGS. 2A to 2D illustrate a mechanism for securing the components of the surgical device according to an embodiment of the disclosure.

FIGS. 2A to 2D illustrate a mechanism for securing the absorbent discs and the spacers onto the handle according to an embodiment of the disclosure. FIG. 2A shows the second part 108 of the handle 102 with two legs 200a and 200b. In this figure, the legs 200a and 200b are shown in an unflexed or uncompressed state. In this state, the legs 200a and 200b form a distance 202 from the tip of the leg 200a to the tip of the leg 200b. The distance 202 is larger than the inner diameter of the absorbent discs and the spacers such that when the absorbent discs and the spacers are placed onto the second part 108, they cannot slip past the legs 200a and 200b and become loose from the second part 108.

Figure 2B:
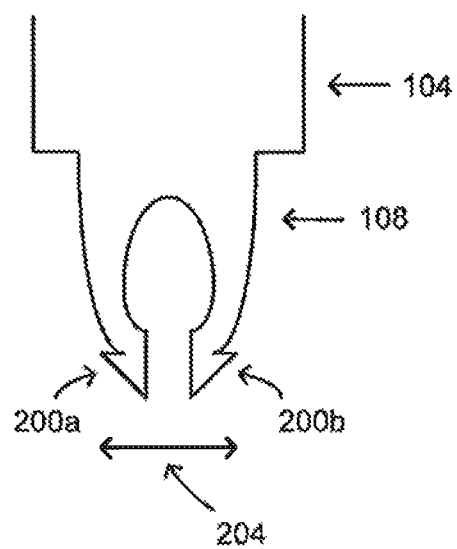
Figure 2C:
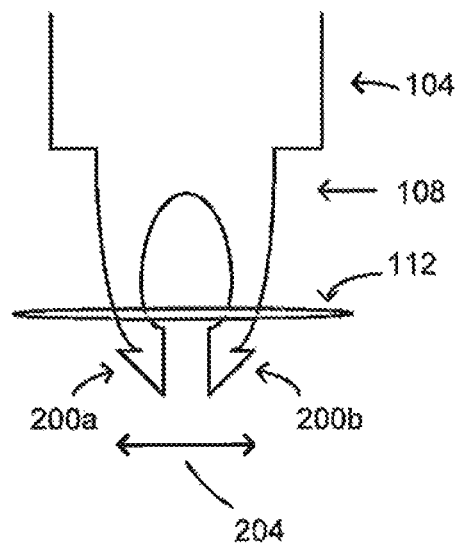
Figure 2D:
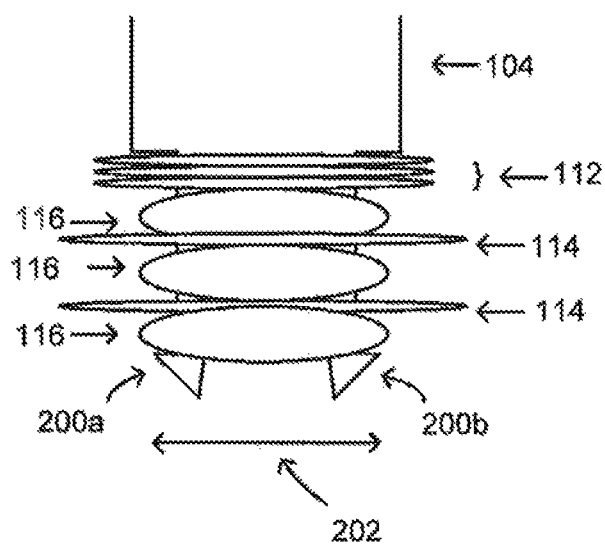

FIG. 2B shows the legs 200a and 200b in a flexed or a compressed state. In this state, the legs 200a and 200b form a distance 204 from the tip of the leg 200a to the tip of the leg 200b. The distance 204 is smaller than the inner diameter of the absorbent discs and the spacers and allows the absorbent discs and the spacers to be placed onto the second part 108. FIG. 2C illustrates a first absorbent disc 112 being placed onto the second part 108 by compressing the legs 200a and 200b to a distance 204 and slipping the first absorbent disc 112 past the two legs 200a and 200b. Once all of the desired absorbent discs and spacers have been placed onto the second part 108, the legs 200a and 200b are released and return to their unflexed or uncompressed state as shown in FIG. 2D. In this state, the legs 200a and 200b maintain the distance 202 from the tip of the leg 200a to the tip of the leg 200b. This prevents the absorbent discs and the spacers from slipping past the legs 200a and 200b and becoming loose from the second part 108.

Although the use of the legs 200a and 200b is shown as one embodiment for securing the absorbent discs and the spacers onto the second part 108 of the handle 102, one of ordinary skill in the art would recognize that alternate methods or systems for securing the absorbents discs and the spacers onto the second part 108 may be used including the use of adhesives.

Figure 3A:
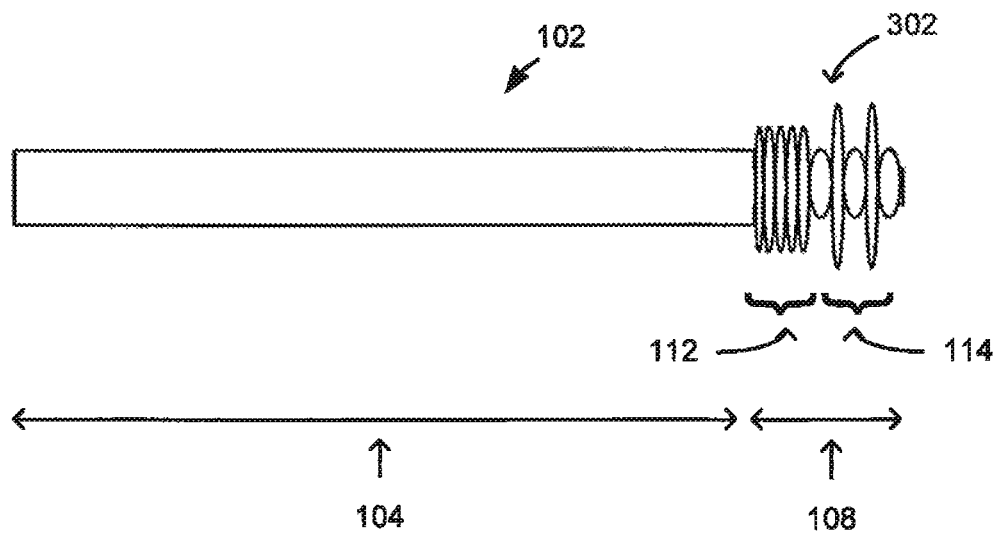
Figure 3B:
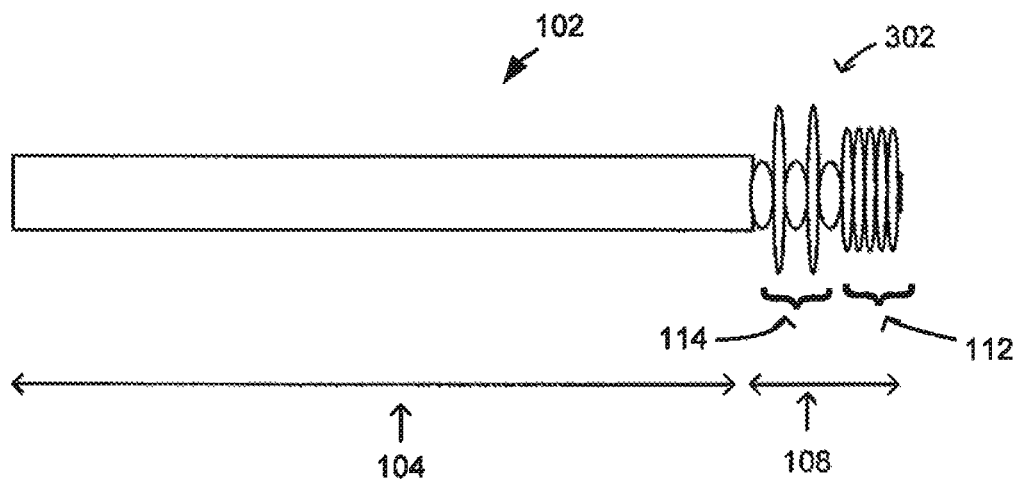

FIGS. 3A to 3C illustrate embodiments of the disclosure having an absorbent area at one end of the surgical device. In FIG. 3A, an absorbent area 302 is formed along the second part 108 of the handle 102. In this embodiment, the absorbent area 302 is formed by placing a plurality of first absorbent discs 112 along the inner portion of the second part 108. A plurality of second absorbent discs 114 is then placed along the outer portion of the second part 108. The plurality of second absorbent discs 114 are separated by spacers 116. The spacers 116 provide the separation that allows the edges of the second absorbent discs 114 to bend and flex. The advantage of this particular embodiment is that the larger second absorbent discs 114 are the first to contact any fluid materials along the trocar. Therefore, the larger absorbent discs 114 will absorb the bulk of the fluid materials as the surgical device is inserted inside the trocar. The plurality of first absorbent discs 112 will follow behind and absorb any fluid materials that are not absorbed by the plurality of absorbent discs 114. In FIG. 3B, the absorbent area 302 is formed by placing the plurality of second absorbent discs 114 along the inner portion of the second part 108 and the plurality of first absorbent discs 112 along the outer portion of the second part 108. Again, the plurality of second absorbent discs 114 are separated by spacers 116 to allow flexibility along the edges of the plurality of second absorbent discs 114. The advantage of this particular embodiment is that the larger absorbent discs 114 will follow behind the smaller first absorbent discs 112 and provide more than sufficient absorbency to absorb any fluid materials that are not absorbed by the plurality of first absorbent discs 112. In FIG. 3C, the absorbent area 302 is formed by placing the plurality of second absorbent discs 114 in the middle of the second part 108 and the plurality of first absorbent discs 112 along the inner and outer portions of the second part 108. By providing a plurality of first absorbent discs 112 before and after the plurality of second absorbent discs 114, this embodiment provides the advantages of the two embodiments shown in FIGS. 3A and 3B.

Figure 4A:
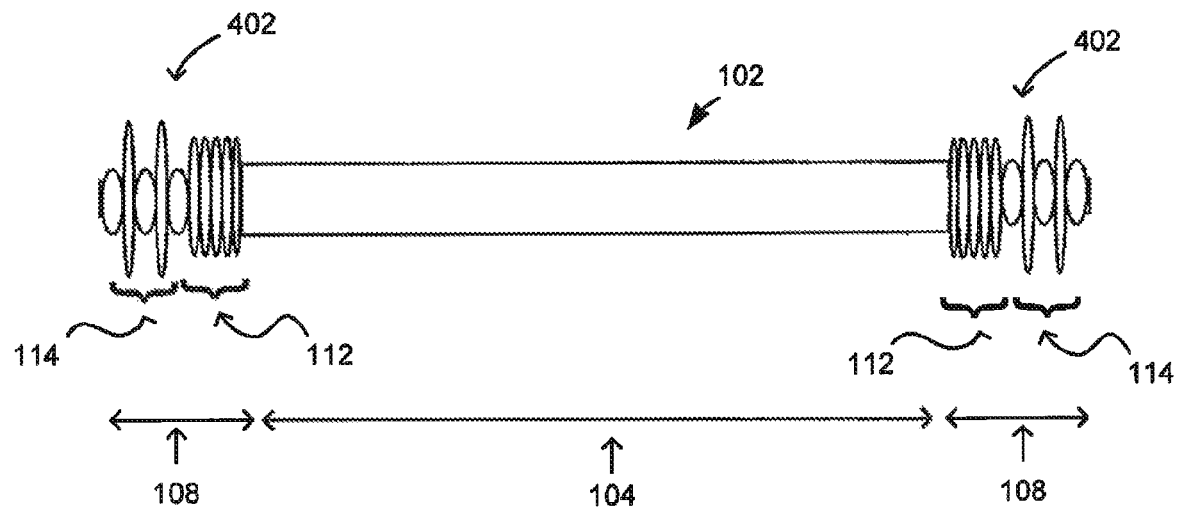
FIGS. 4A and 4B illustrate further embodiments of the disclosure.
Figure 4B:
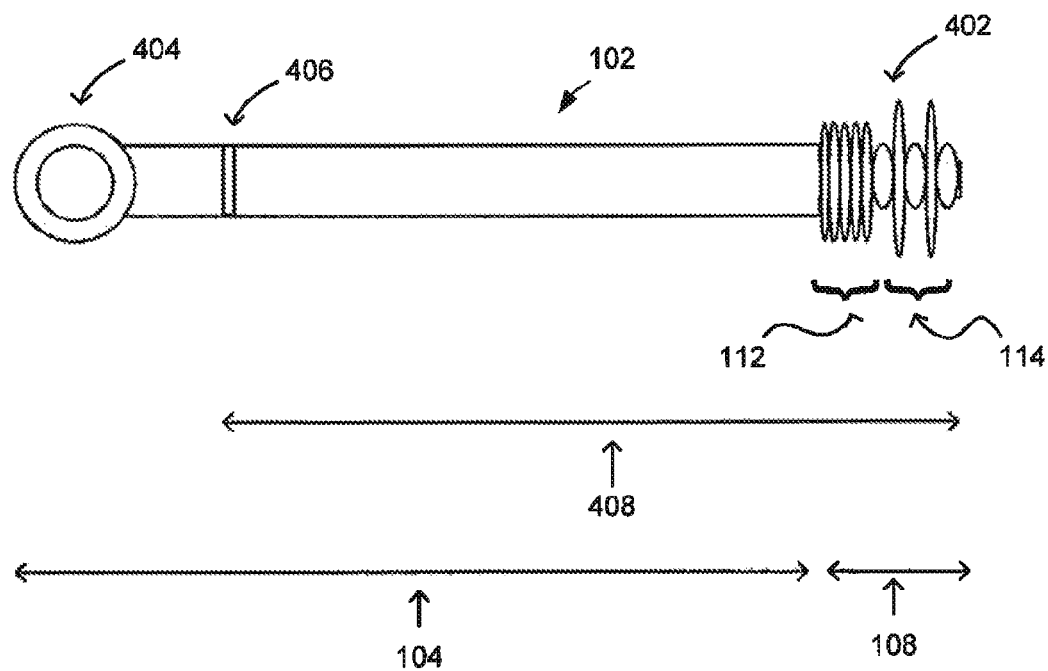

FIGS. 4A and 4B illustrate further embodiments of the disclosure. In FIG. 4A, the surgical device is shown as having an absorbent area 402 at both ends of the handle 102. In FIG. 4B, a grip 404 is provided at an end of the handle 102. The grip 404 may be formed as an integral part of the handle 102 or may be formed separately from the handle 102. The grip 404 is formed, for example, from a type of plastic that is commonly used in many surgical instruments. The grip 404 makes it easier to use the surgical device by providing a means for holding the surgical instrument. A marker 406 is also shown in this embodiment. The marker 406 is used to indicate an optimal distance 408 for inserting the cleaning instrument inside a trocar. Such a distance is far enough to allow any fluid along the outer wall of the distal tip of a trocar to be absorbed without being inserted so far that the absorbent discs of the surgical device become saturated by coming into significant contact with fluid material that is not gathered on the trocar surfaces. Significant contact may be taken as having more than fifty percent of the absorbed fluid materials come from contact with bodily fluids that are not gathered on the surfaces of the trocar. For example, the optimal distance may be from 28 to 30 cm for a trocar with a length of 29 cm.

Although the above embodiments describe absorbent discs as one way of forming an absorbent area on the surgical device, one of ordinary skill in the art would recognize that alternate systems and methods of providing an absorbent surface along the valves, the inner wall, and the tip of the trocar may be used. For example, the absorbent area could be formed with a continuous absorbent surface along its exterior. Furthermore, one of ordinary skill in the art would also recognize that any method or system for removing fluid materials from the surfaces of the trocar could be used. For instance, inserting a surface that pushes or squeezes, rather than actually absorbing, the fluid materials from the surfaces could also be used. As one example, a water-repellant area may be formed by a plurality of rubber, or other water-resistant, discs. These water-resistant discs would have flexibility along their edges that would allow them to bend and flex along the surfaces of the trocar with a proximity that was close enough to push or squeeze any fluid materials from a surface or multiple surfaces of the trocar. Also, while the above embodiments describe a bead as one way of separating the absorbent discs, one of ordinary skill in the art would recognize that alternate systems and methods of providing separation between the absorbent discs may be used. For example, one could separate the second absorbent discs 114 simply by placing one or more of the first absorbent discs 112 between each of the second absorbent discs 114. Furthermore, while the above embodiments disclose specific orientations of the absorbent discs and the spacers, one of ordinary skill in the art would recognize that any number and/or combination of the absorbent discs and the spacers may be used. For example, spacers could also be placed between the first absorbent discs 112 as well as the second absorbent discs 114.

As stated earlier, fluid materials become deposited on the surfaces of a trocar once it is inserted across an abdominal wall. As shown in FIG. 5, fluid materials 512 have become deposited along an outer valve 502, an inner valve 504, an inner wall 506, and an outer wall 508 of the distal tip 510 of a trocar 500 after it has been inserted across an abdominal wall 514. The distal end or tip for the purposes of this disclosure refers to the end of the trocar that is inserted into the body cavity. In this embodiment, the trocar has an inner diameter 516 and an outer diameter 518.

Figure 6:
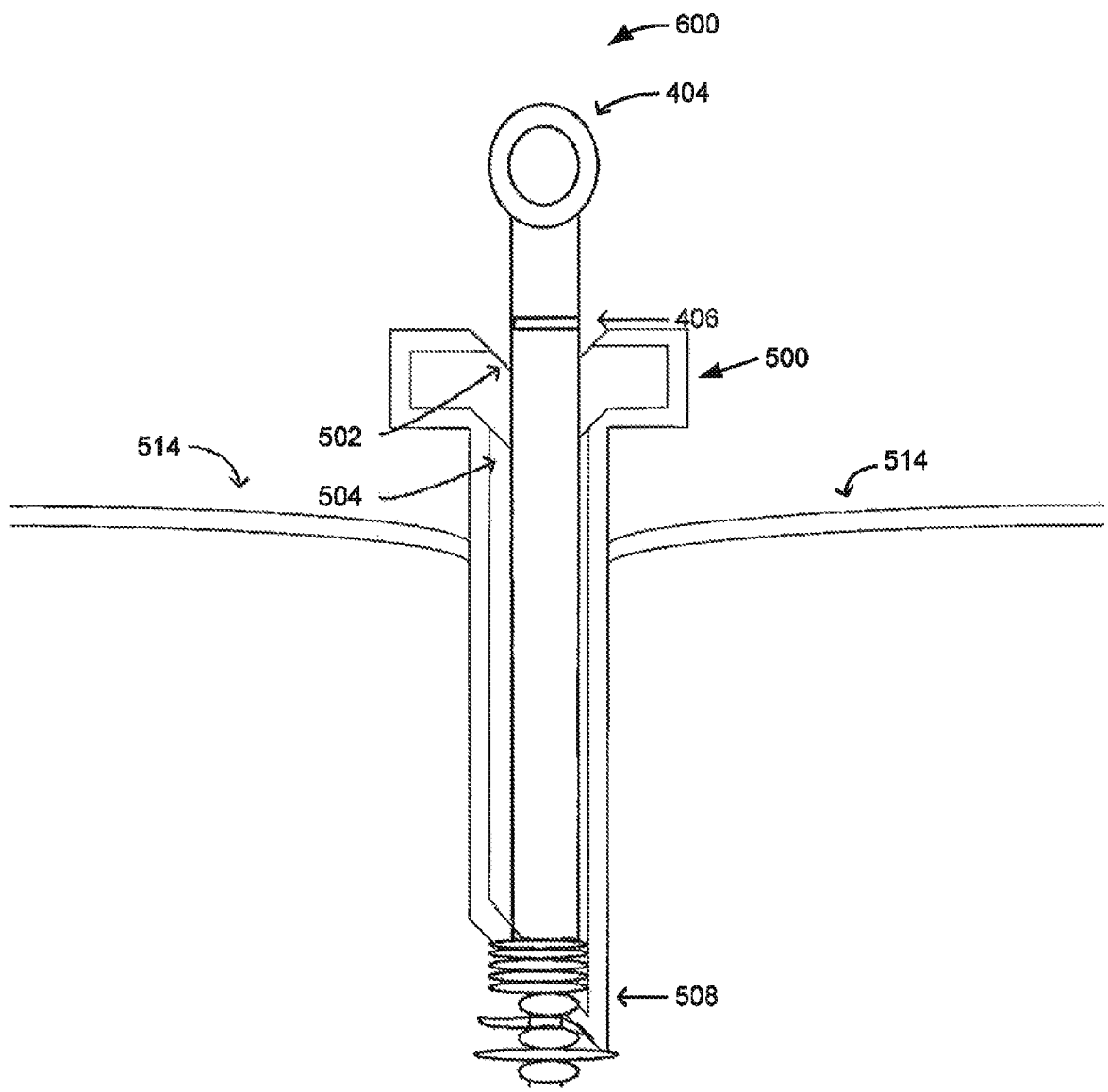
FIG. 6 is an illustration of a surgical device according to an embodiment of the disclosure.

FIG. 6 is an illustration of a surgical device according to an embodiment of the disclosure. In this embodiment, a fluid absorbent surgical device 600 is inserted into the trocar 500. The surgical device 600 has been inserted beyond the outer valve 502 and the inner valve 504 of the trocar 500 and has absorbed the fluid materials 512 along the two valves. The surgical device 600 has also been inserted along the inner wall 506 of the trocar 500 and has also absorbed the fluid materials 512 along the inner wall 506. As shown in this embodiment, the plurality of first absorbent discs 112 has an outer diameter that is larger than the inner diameter 516 of the trocar 500. This allows the edges of the plurality of first absorbent discs 112 to sweep the inner wall 506 and absorb any fluid materials 512 that is along the inner wall 506. The plurality of second absorbent discs 114 are shown as having an outer diameter that is larger than the outer diameter of the trocar 500. This provides the outer edges of the plurality of second absorbent discs 114 with the length needed to absorb the fluid materials 512 along the outer wall 508 of the tip 510 of the trocar 500. The marker 406 is used to indicate an optimal distance for inserting the surgical device 600 inside the trocar 500. As stated earlier, the optimal distance is far enough to allow any fluid along the outer wall of the tip 510 to be absorbed without being inserted so far that the absorbent discs of the surgical device become saturated by coming into significant contact with fluid material that is not gathered on the trocar surfaces. Again, significant contact may be taken as having more than fifty percent of the absorbed fluid materials come from contact with bodily fluids that are not gathered on the surfaces of the trocar.

Figure 7:
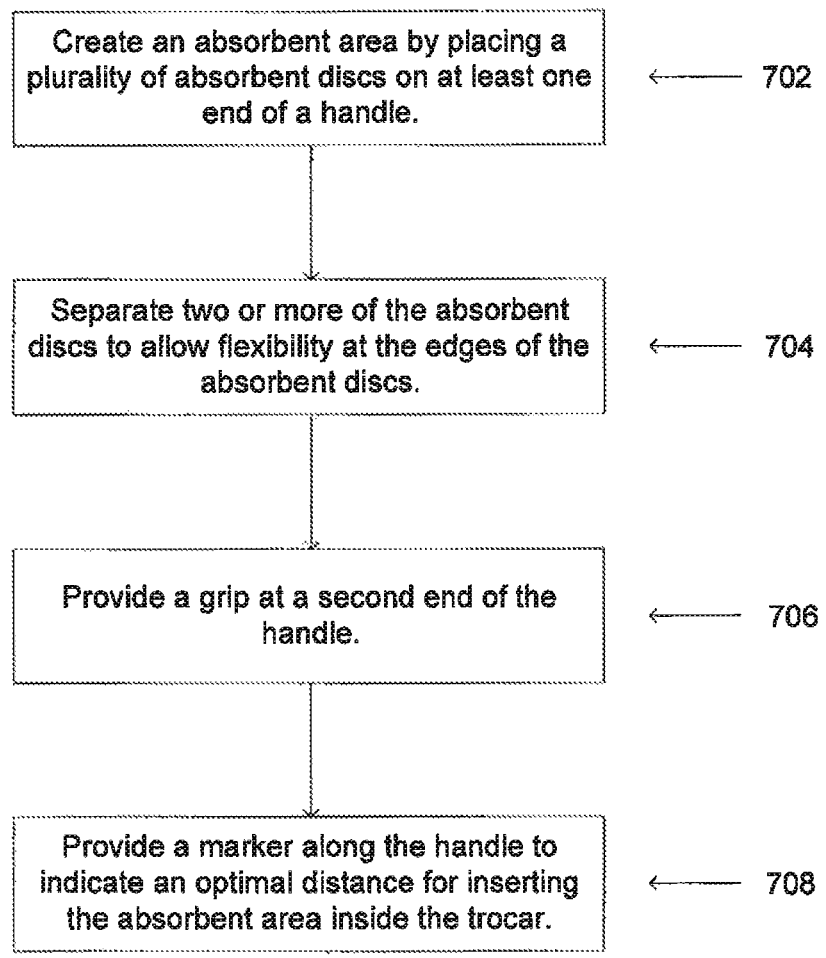
FIG. 7 illustrates a method of making a fluid absorbent surgical device according to an embodiment of the disclosure.

FIG. 7 illustrates a method of making a fluid absorbent surgical device according to an embodiment of the disclosure. In this embodiment, an absorbent area is created by placing a plurality of absorbent discs on at least one end of a handle (block 702). The plurality of absorbent discs includes a first group of absorbent discs having an outer diameter that is larger than the inner diameter of the trocar to be swept. The plurality of absorbent discs also includes a second group of absorbent discs having an outer diameter that is larger than the outer diameter of the trocar. Two or more discs of the second group of absorbent discs are separated to allow flexibility at the edges of the absorbent discs (block 704). A grip is provided at a second end of the handle (block 706). A marker is also provided along the handle to indicate an optimal distance for inserting the absorbent area inside the trocar (block 708).

Figure 8:
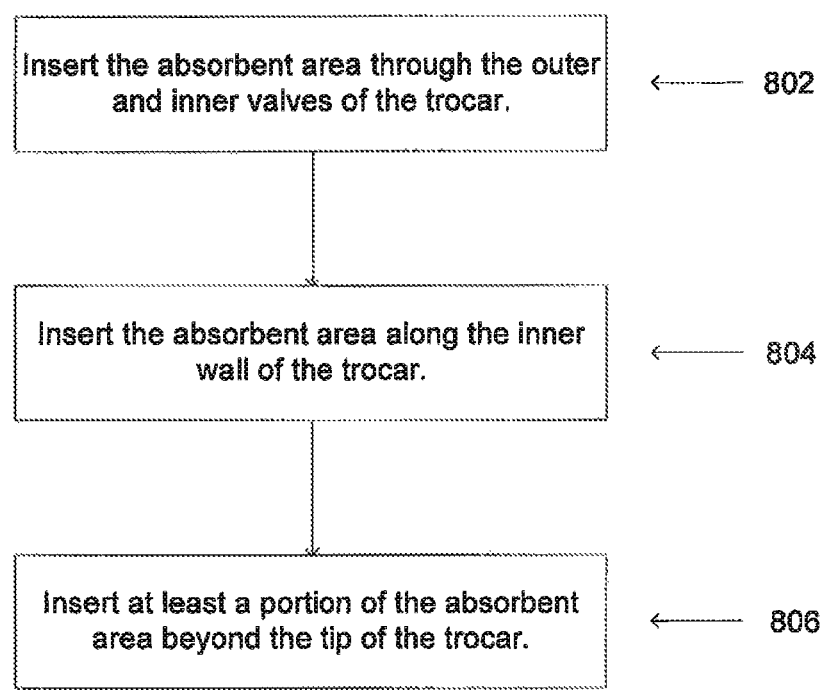
FIG. 8 illustrates a method of sweeping the trocar using a surgical device according to an embodiment of the disclosure.

FIG. 8 illustrates a method of sweeping the trocar using a surgical device according to an embodiment of the disclosure. In this embodiment, the trocar is swept by inserting the absorbent area through the outer and inner valves of the trocar (block 802). This will absorb any fluid materials along the inner and outer valves. The inner wall of the trocar is also swept by inserting the absorbent area along the inner wall of the trocar (block 804). Because the absorbent area will have an outer diameter larger than the inner diameter of the trocar, the edges of the absorbent area will brush along the inner walls of the trocar and absorb any fluid materials along the inner walls. The outer wall along a distal tip of the trocar is also swept by inserting at least a portion of the absorbent area past the tip of the trocar (block 806). Because at least part of the absorbent area that is inserted beyond the tip of the trocar has a larger diameter than the outer diameter of the trocar, the edges of the absorbent area will extend beyond the tip of the trocar and absorb fluid materials along the outer wall of the tip of the trocar.

Figure 9:
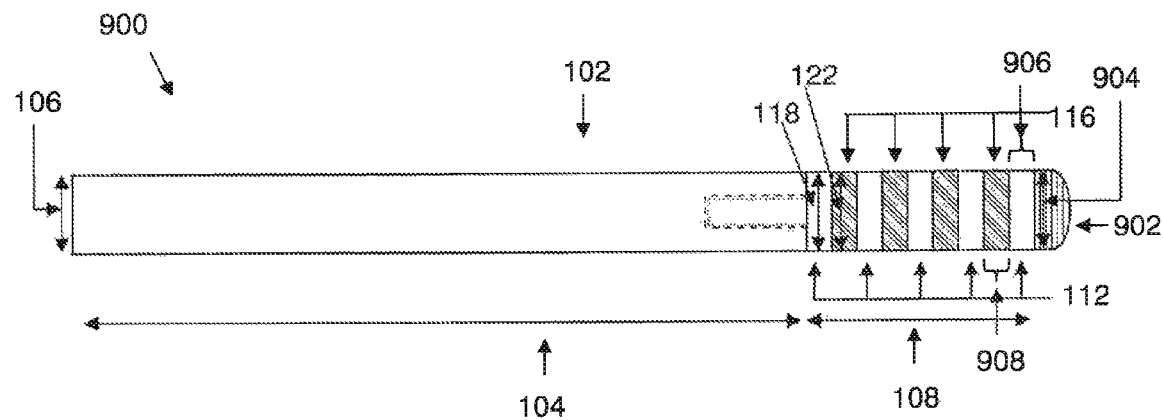
FIG. 9 illustrates a surgical device according to an embodiment of the disclosure.

FIG. 9 illustrates another embodiment of a fluid absorbent surgical device 900. The fluid absorbent surgical device 900 illustrated in FIG. 9 may comprise a handle 102 having a first part 104 and a second part 108, a plurality of first absorbent disks 112, a plurality of spacers 116, and an end cap 902. In an embodiment, the first part 104 of the handle 102 may be approximately 20 cm in length with a diameter of 5 mm and the second part 108 of the handle 102 may be approximately 2 cm in length with a diameter of 3 mm. As indicated by the dashed lines, the second part 108 of the handle 102 may be inserted into the first part 104 of the handle 102 and secured with an adhesive. Including the second part 108 of the handle 102 that is inserted into the first part 104, the second part 108 may be approximately 5.0 cm in length.

The plurality of first absorbent discs 112 and the plurality of spacers 116 may be inserted onto the second part 108 of the handle 102. The end cap 902 may secure the plurality of first absorbent discs 112 and the plurality of spacers 116 on the handle 102. In an embodiment, the end cap 902 is made of plastic. Alternatively, the end cap 902 may be made of sterile cotton or foam or some other material. The end cap 902 may be rounded to enable easier and smoother transition of the fluid absorbent surgical device 900 into and out of the trocar.

In an embodiment, as is illustrated in FIG. 9, the plurality of first absorbent discs 112 and the plurality of spacers 116 are alternated starting and ending with a first absorbent disc 112. Separating each of the plurality of first absorbent discs 112 with at least one of the plurality of spacers 116 may help to limit expansion of the plurality of first absorbent discs 112 as well as reduce leakage of the collected fluid material from the plurality of absorbent discs 112. While five first absorbent discs 112 and four spacers 116 are shown in FIG. 9 alternated with each other, one of ordinary skill will appreciate that any number of first absorbent discs 112 and spacers 116 may be inserted onto the second part 108 of the handle 102 in a number of different orientations without departing from the scope of the disclosure.

The outer diameter 118 of the plurality of first absorbent discs 112 may approximate the inner diameter of the trocar through which the fluid surgical device 900 is going to be inserted such that the outer diameter 118 of the plurality of absorbent discs 112 can come into contact with a meniscus of a drop of fluid residing on the inner surface of the trocar thereby allowing absorbance of the drop of fluid. Similarly, the outer diameter 122 of the plurality of spacers 116 may also approximate the inner diameter of the trocar through which the fluid surgical device 900 is going to be inserted. In an embodiment, the outer diameter 118 of the plurality of first absorbent discs 112 and/or the outer diameter 122 of the plurality of spacers 116 approximating the inner diameter of the trocar means that the first absorbent discs 112 and/or the plurality of spacers 116 are of a size such that they come into contact with the inside of the trocar when inserted therein. In another embodiment, the outer diameter 118 of the plurality of first absorbent discs 112 and/or the outer diameter 122 of the plurality of spacers 116 approximating the inner diameter of the trocar means that the plurality of first absorbent disks 112 and/or the plurality of spacers 116 are of a size such that they do not have to come into full contact with the trocar when inserted therein. For example, the outer diameter 118 of the plurality of first absorbent discs 112 and/or the outer diameter 122 of the plurality of spacers 116 may be slightly less than the inside of the diameter of the trocar. Such an embodiment is enabled by capillary action. Stated differently, capillary action may enable the plurality of first absorbent discs 112 to absorb the fluid materials inside the trocar without contacting the inside of the trocar.

As illustrated in FIG. 9, the outer diameter 118 of the plurality of first absorbent discs 112 and the outer diameter 122 of the plurality of spacers 116 may be approximately equivalent to the first diameter 106 of the handle 102. Additionally, the end cap 902 may comprise an outer diameter 904 that is approximately equivalent to the first diameter 106 of the handle 102. For example, the outer diameters of the first absorbent discs 112, the plurality of spacers 116, and/or the end cap 902 may be approximately 5 mm. Having the outer diameters of the first absorbent discs 112, the plurality of spacers 116, and/or the end cap 902 be approximately equivalent creates a fluid absorbent surgical instrument 900 with a smooth surface, which helps to reduce the likelihood of the fluid absorbent surgical instrument 900 catching an edge of the trocar and pulling the trocar out of the body.

In some embodiments, the outer diameter 118 of the plurality of first absorbent discs 112 may be slightly smaller than the outer diameter 122 of the plurality of spacers 116. In such embodiments, capillary action may enable the plurality of first absorbent discs 112 to absorb the fluid from the inside surface of the trocar. Also, such embodiments may enable the plurality of first absorbent discs 112 to expand if necessary after absorbing the fluid without allowing the plurality of first absorbent discs 112 to expand beyond the outer diameter 122 of the plurality of spacers 116 thereby reducing the likelihood that the plurality of first absorbent discs 112 will leak absorbed fluids as the fluid absorbent surgical device 900 is pulled out of the trocar.

In an embodiment, as is illustrated in FIG. 9, the thickness 906 of the plurality of first absorbent discs 112 and the thickness 908 of plurality of spacers 116 are approximately equivalent. For example, the thickness 906 of the plurality of first absorbent discs 112 and the thickness 908 of the plurality of spacers 116 may be approximately 3 mm. Alternately, the thickness 908 of plurality of spacers 116 may be greater than or less than the thickness 906 of the plurality of first absorbent discs 112.

The plurality of first absorbent discs 112 may be made of an absorbent material. In a preferred embodiment, the plurality of first absorbent discs 112 are made of an absorbent material with minimal expansion. Such an embodiment avoids redistribution or leaking of the collected fluid materials from the plurality of first absorbent discs 112 as the fluid absorbent surgical device 900 is being moved through the trocar. Additionally, such an embodiment helps to reduce the chances that one of the plurality of first absorbent discs 112 will expand to such degree that it catches an edge of the trocar and causes the trocar to be pulled from the body. In an embodiment, the plurality of first absorbent discs 112 are made of foam. Specifically, the plurality of first absorbent discs 112 may be made of polyvinyl acetyl (PVA) foam. Alternatively, the plurality of first absorbent discs 112 may be made of sterile cotton or some other absorbent material.

The plurality of spacers 116 may be discs made of a non-absorbent material. For example, in an embodiment, the plurality of spacers 116 are made of a type of plastic that is commonly used in many surgical instruments. Thus, in some embodiments, the plurality of spacers 116 may be considered a plurality of non-absorbent discs.

Figure 10A:
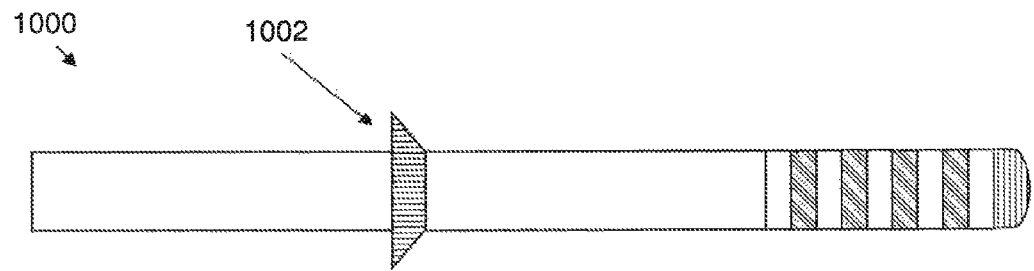
FIGS. 10A and 10B illustrate a surgical device according to an embodiment of the disclosure.
Figure 10B:
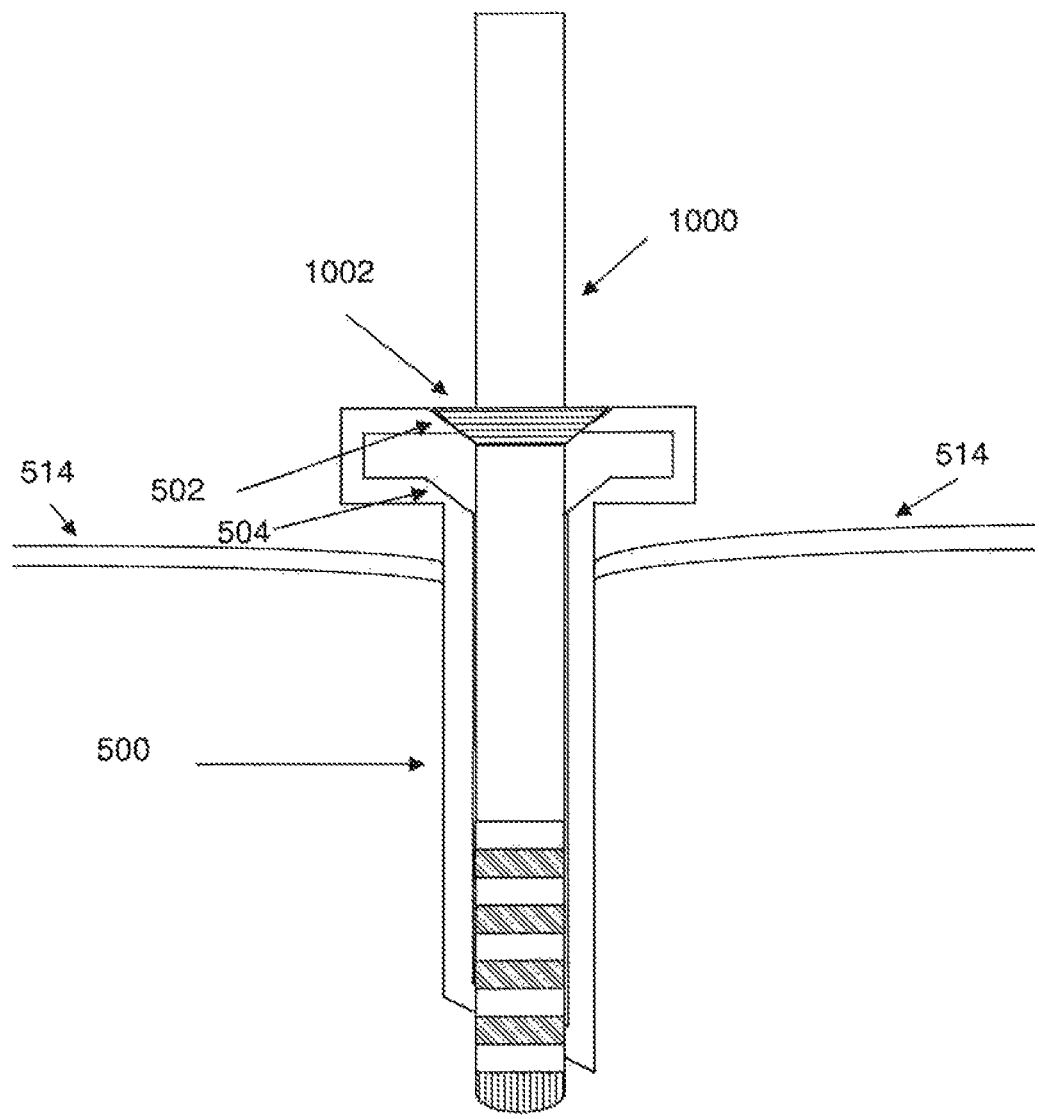

FIGS. 10A and 10B illustrate another embodiment of a fluid absorbent surgical device 1000. In an embodiment, the fluid absorbent surgical device 1000 is similar to the fluid absorbent surgical device 900 illustrated in FIG. 9 except that the fluid absorbent surgical device 1000 also comprises a wedge 1002. The wedge 1002 may be a part of the first part 104 of the handle 102 or may be an addition to the first part 104 of the handle 102.

In an embodiment, the wedge 1002 is positioned on the handle 102 to indicate an optimal distance for inserting the fluid absorbent surgical device 1000 inside the trocar 500. Referring to FIG. 10B, the wedge 1002 may be shaped such that it is not capable or not easily capable of being pushed through the outer valve 502. For example, the wedge 1002 may act as a stopper hindering and/or preventing the fluid absorbent surgical device 1000 from moving any further through the trocar 500 once the wedge 1002 contacts the outer valve 502.

As is shown in FIG. 10B, in some embodiments, the wedge 1002 may be positioned on the handle 102 such that one or more of the plurality of first absorbent discs 112 and/or one or more of the of plurality of spacers 116 are capable of protruding beyond the tip of the trocar 500. Such an embodiment may enable the fluid absorbent surgical device 1000 to absorb fluid from the outer wall along a distal tip of the trocar 500. In other embodiments, the wedge may be positioned on the handle 102 such that none of the plurality of first absorbent discs 112 or the plurality of spacers 116 are capable of protruding beyond the tip of the trocar 500.

The wedge 1002 may be made out of an absorbent material such as foam or cotton thereby enabling the wedge 1002 to absorb fluids that have become deposited along the outer valve 502. Alternatively, the wedge 1002 may be made of a non-absorbent material such as a type of plastic that is commonly used in many surgical instruments.

Figure 11A:
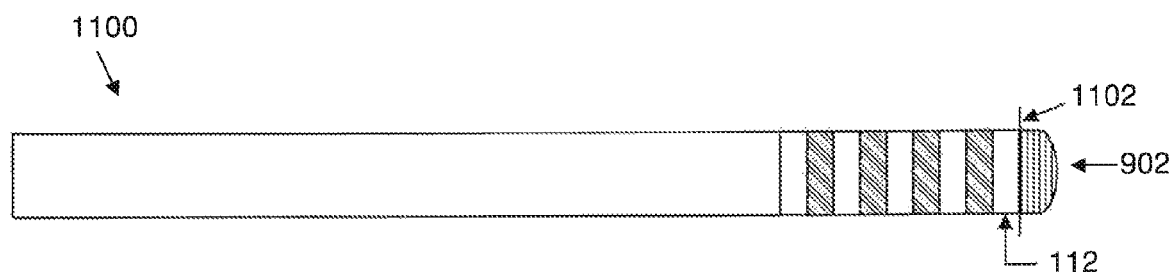
FIGS. 11A to 11C illustrate a surgical device according to an embodiment of the disclosure.
Figure 11B:
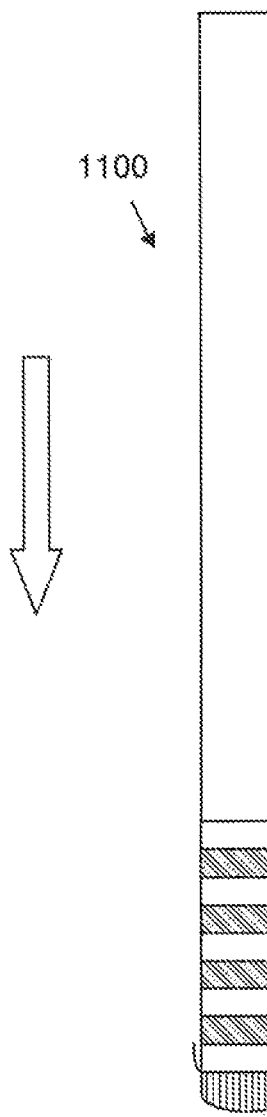
Figure 11C:
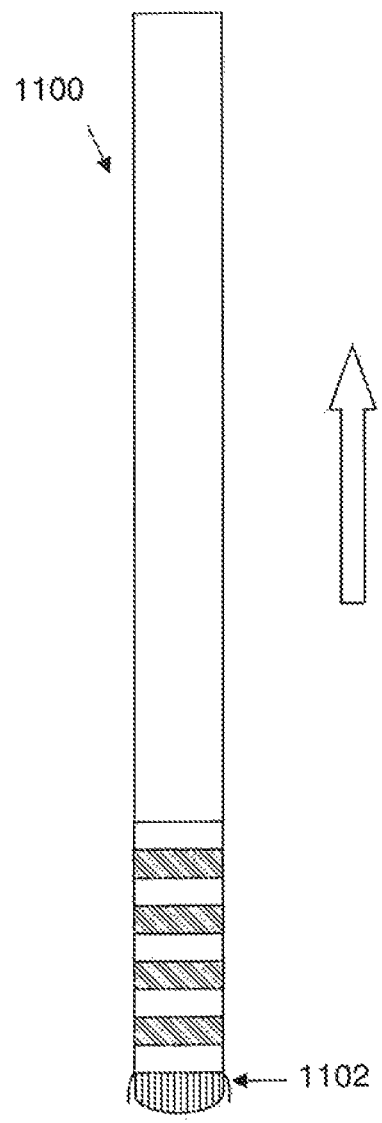

FIGS. 11A to 11C illustrate another embodiment of a fluid absorbent surgical device 1100. In an embodiment, the fluid absorbent surgical device 1100 is similar to the fluid absorbent surgical device 900 illustrated in FIG. 9 except that the fluid absorbent surgical device 1100 also comprises a third disc 1102. The third disc 1102 may be positioned on the outer portion of the second part 108. For example, the third disc 1102 may be positioned between a first absorbent disc 112 and the end cap 902.

In an embodiment, the third disc 1102 is made of a flexible material that enables the third disc 1102 to dome or fold. For example, the third disc 1102 may be made of a flexible non-absorbent material such as plastic.

As to the size of the third absorbent disc, in an embodiment, the third disc 1102 comprises a diameter that is larger than the inside diameter of the trocar. For example, the third disc 1102 may comprise a diameter that is greater than or equal to the outside diameter of the trocar. Additionally, the third disc 1102 may comprise a thickness that enables the third disc to flex around at least part of the first absorbent disc 112 as the fluid absorbent surgical device is inserted into the trocar (illustrated in FIG. 11B) and at least part of the end cap 902 as the fluid absorbent surgical device 1100 is removed from the trocar (illustrated in FIG. 11C). For instance, the third disc 1102 may be thinner than the plurality of first absorbent discs 112 and the plurality of spacers 116. In some embodiments, although not illustrated in FIGS. 11A to 11C, the diameter of the first absorbent disc 112 and the end cap 902 may be reduced in order to allow the third disc 1102 to fold around the first absorbent disc 112 and the end cap 902 as the fluid absorbent surgical device 1100 is inserted into and pulled out of the trocar. Also, in some embodiments, although not illustrated in FIGS. 11A to 11C, the thickness of the first absorbent disc 112 may be reduced to enable the third disc 1102 to cover most or the entire first absorbent disc 112.

Referring to FIG. 11B, as the fluid absorbent device 1100 is inserted into the trocar, the third disc 1102 may shield or cover some or significantly all of the first absorbent disc 112 thereby protecting the first absorbent disc 112 and keeping the first absorbent disc 112 at least partially non-saturated. This may prevent over saturation of the first absorbent disc 112 and the leaking of absorbed fluids as the fluid absorbent surgical device 1100 is pulled out of the trocar.

Referring to FIG. 11C, as the fluid absorbent device 1100 is pulled out of the trocar, the third disc 1102 may flex in the opposite direction around the end cap 902 thereby exposing the first absorbent disc 112. In an embodiment, since the first absorbent disc 112 was protected by the third disc 1102 as the fluid absorbent surgical device 1100 was inserted into the trocar, the first absorbent disc 112 is in a non-saturated state that enables it to collect or scavenge the remaining fluid as the fluid absorbent surgical device 1100 is pulled out of the trocar. While only illustrated in FIGS. 11A-11C as a single third disc 1102, one of ordinary skill in the art will appreciate that the fluid absorbent surgical device may comprise a plurality of third absorbent discs without departing from the scope of the disclosure.

Figure 12:
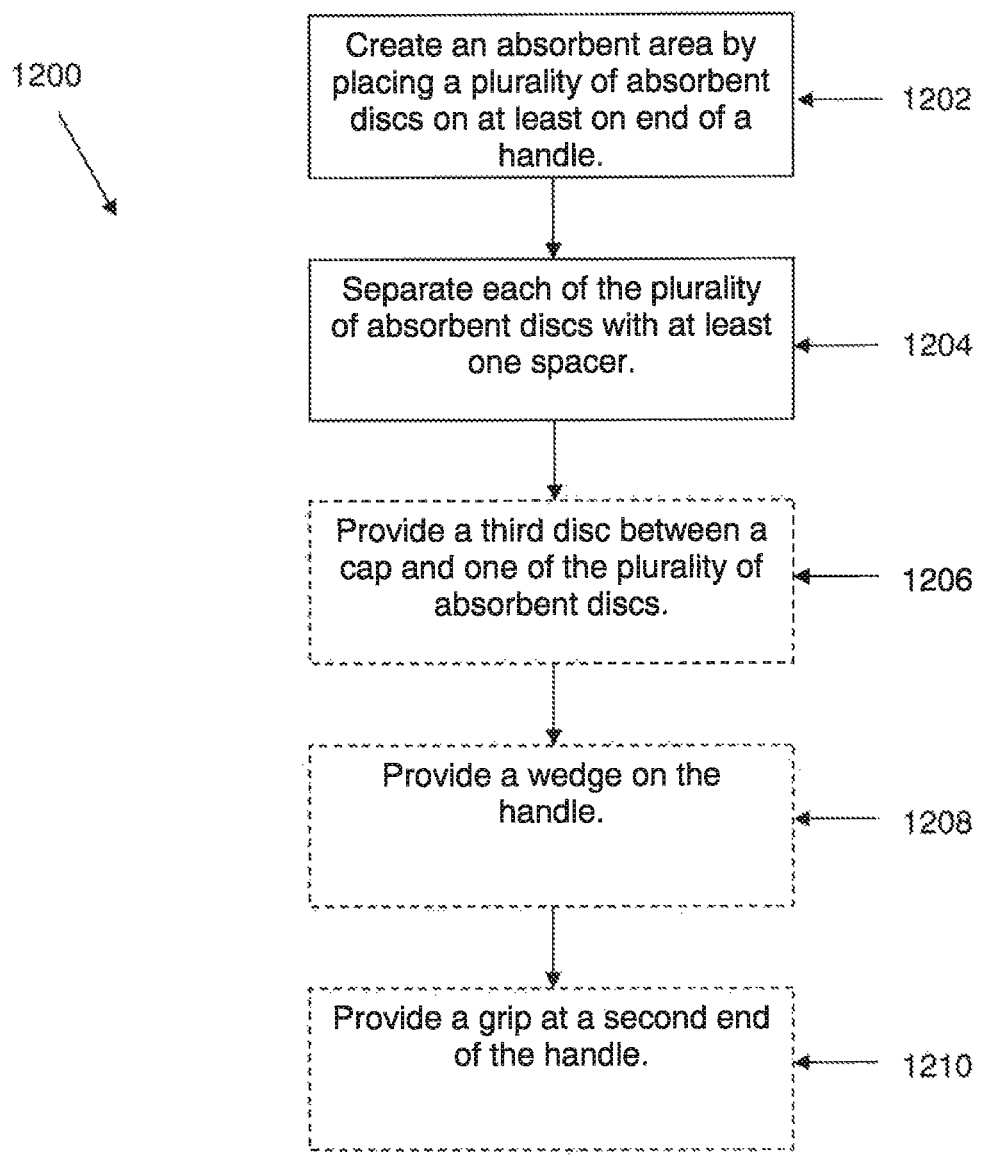
FIG. 12 illustrates a method of making a fluid absorbent surgical device according to an embodiment of the disclosure.

FIG. 12 illustrates a method 1200 of making a fluid absorbent surgical device according to an embodiment of the disclosure. In this embodiment, an absorbent area is created by placing a plurality of absorbent discs on at least one end of a handle (block 1202). Each of the plurality of absorbent discs may be separated by at least one spacer of a plurality of spacers (block 1204). In an embodiment, the plurality of absorbent discs and the plurality of spacers are approximately equivalent in size (e.g., diameter, thickness, etc.). A third disc may be provided between an end cap and one of the plurality of absorbent discs to shield the one of the plurality of absorbent discs as the fluid absorbent surgical device is inserted into the trocar (block 1206). In an embodiment, the third disc is made a flexible non-absorbent material and is larger in diameter than the plurality of absorbent discs and the plurality of spacers, but smaller in thickness than the plurality of absorbent discs and the plurality of spacers. A wedge may be provided on the handle to indicate an optimal distance for inserting the absorbent area into the trocar (block 1208). A grip may be provided at a second end of the handle (block 1210). Blocks 1206-1210 may be optional as indicated by the hashed boxes.

While a number of the embodiments described above disclose the fluid absorbent surgical device comprising a plurality of absorbent discs, in alternate embodiments, the fluid absorbent surgical device may comprise a plurality of linear strips of absorbent material secured to the handle 102 in addition to or in lieu of the plurality of absorbent discs. The plurality of linear strips of absorbent material may be secured to the handle 102 using an adhesive. In another alternative embodiment, in addition to or in lieu of the plurality of absorbent discs, the second part 108 of the handle 102 may be fenestrated and absorbent material may be placed inside the second part 108 of the handle 102. For example, the second part 108 of the handle 102 may comprise a plurality of holes. In such an alternative embodiment, as the fluid absorbent surgical device is inserted through a trocar, the fluid material may be pulled into the plurality of holes of the second part 108 of the handle 102 by capillary action and the absorbent material inside the second part 108 of the handle 102 may hold or absorb the fluid material.

Although the use of the surgical device of the disclosure is described in the context of laparoscopic surgery, one of ordinary skill in the art would recognize that it could also be used in other endoscopic or minimally invasive procedures, such as thoracoscopic surgery.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

Also, techniques, systems, subsystems and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

What is claimed is:

1. A surgical instrument that absorbs fluid material on surfaces of a cannula, comprising:
   a handle having a first end, a second end, and a central, longitudinal axis extending between the first end and the second end of the handle; and
   an absorbent area at the first end of the handle, wherein the absorbent area comprises a plurality of absorbent discs and a plurality of non-absorbent spacers, wherein each of the plurality of absorbent discs has an outer diameter that is approximately equivalent to an outer diameter of each of the plurality of non-absorbent spacers, wherein each of the plurality of absorbent discs has a longitudinal thickness that is approximately equivalent to each of the plurality of non-absorbent spacers along the central, longitudinal axis of the handle, and wherein the longitudinal thickness of each of the plurality of discs and each of the plurality of non-absorbent spacers is less than the outer diameter of each of the plurality of absorbent discs and each of the plurality of non-absorbent spacers.

2. The surgical instrument of claim 1, wherein the cannula is used to insert an endoscope into a body cavity.

3. The surgical instrument of claim 1, wherein each of the plurality of absorbent discs is separated by at least one of the plurality of non-absorbent spacers.

4. The surgical instrument of claim 1, wherein the first end of the handle comprises a round end cap, and wherein the absorbent area at the first end of the handle further comprises a non-absorbent disc positioned between the round end cap and one of the plurality of absorbent discs.

5. The surgical instrument of claim 4, wherein the non-absorbent disc comprises a larger diameter and a smaller thickness than the plurality of absorbent discs and the plurality of non-absorbent spacers, and wherein the non-absorbent disc shields the one of the plurality of absorbent discs as the surgical instrument is inserted into the cannula and exposes the one of the plurality of absorbent discs as the surgical instrument is removed from the cannula thereby allowing the one of the plurality of absorbent discs to collect remaining fluid material as the surgical instrument is removed from the cannula.

6. The surgical instrument of claim 1, wherein each of the plurality of non-absorbent spacers is a non-absorbent disc.

7. The surgical instrument of claim 1, wherein each of the plurality of absorbent discs is one of sterile cotton discs and foam discs.

8. The surgical instrument of claim 7, wherein the foam discs are made of polyvinyl acetyl foam.

9. The surgical instrument of claim 1, wherein the absorbent area is configured to be inserted into the cannula to absorb fluid on one or more surfaces of the cannula.

10. The surgical instrument of claim 1, wherein each of the plurality of non-absorbent spacers is secured to the handle.

11. The surgical instrument of claim 10, wherein each of the plurality of non-absorbent spacers is secured to the handle using one or more adhesives.

12. A surgical instrument that absorbs fluid material on surfaces of a cannula, comprising:
a handle having a first end, a second end, and a central, longitudinal axis extending between the first end and the second end of the handle; and
an absorbent area at the first end of the handle, wherein the absorbent area comprises a plurality of absorbent discs and a plurality of non-absorbent spacers, wherein each of the plurality of absorbent discs has a shaped disc that is substantially equivalent to each of the plurality of non-absorbent spacers, wherein the shaped disc has a longitudinal thickness along the central, longitudinal axis that is less than an outer diameter of each of the plurality of absorbent discs and each of the plurality of non-absorbent spacers, and wherein the plurality of absorbent discs approximates an inner diameter of the cannula.

13. The surgical instrument of claim 12, wherein each of the plurality of absorbent discs is separated by one of the plurality of spacers.

14. The surgical instrument of claim 12, wherein each of the plurality of absorbent discs is one of sterile cotton discs and foam discs.

15. The surgical instrument of claim 14, wherein the foam discs are made of polyvinyl acetyl foam.

16. The surgical instrument of claim 12, wherein when the absorbent area is inserted inside the cannula, the absorbent area absorbs fluid along the inner wall of the cannula.

17. The surgical instrument of claim 12, wherein the absorbent area is configured to be inserted into the cannula to absorb fluid on one or more surfaces of the cannula.

18. The surgical instrument of claim 12, wherein the plurality of non-absorbent spacers approximates the inner diameter of the cannula, and wherein the plurality of absorbent discs and the plurality of non-absorbent spacers are approximately equivalent in longitudinal thickness along the central, longitudinal axis of the handle.

19. A method of creating a surgical instrument, comprising:
providing an absorbent area on at least one end of a handle, the absorbent area comprising a plurality of absorbent discs and a plurality of non-absorbent spacers, wherein the handle comprises a first end, a second end, and a central, longitudinal axis extending between the first end and the second end of handle; and
separating each of the plurality of absorbent discs with at least one spacer, wherein each of the plurality of absorbent discs has an outer diameter that is approximately equivalent to an outer diameter of each of the at least one spacer, wherein a longitudinal thickness of each of the plurality of absorbent discs and each of the at least one spacer is less than the outer diameter of each of the plurality of absorbent discs and each of the at least one spacer, and wherein the plurality of absorbent discs approximates an inner diameter of a cannula.

20. The method of claim 19, wherein the at least one spacer approximates the inner diameter of the cannula.

* * * * *